(12) United States Patent
Golosarsky et al.

(10) Patent No.: US 8,579,830 B2
(45) Date of Patent: Nov. 12, 2013

(54) NEUROPATHY DIAGNOSTIC DEVICE

(75) Inventors: Boris Golosarsky, Nashua, NH (US);
James Bernhard, Plainville, MA (US);
Michael Brown, Nashua, NH (US);
John McCarthy, Newbury, NH (US)

(73) Assignee: Prosenex, LLC, Hudson, NH (US)

( * ) Notice: Subject to any disclaimer, the term of this patent is extended or adjusted under 35 U.S.C. 154(b) by 313 days.

(21) Appl. No.: 13/054,136

(22) PCT Filed: Jul. 17, 2009

(86) PCT No.: PCT/US2009/004159
§ 371 (c)(1),
(2), (4) Date: Jan. 14, 2011

(87) PCT Pub. No.: WO2010/008592
PCT Pub. Date: Jan. 21, 2010

(65) Prior Publication Data
US 2011/0112431 A1    May 12, 2011

Related U.S. Application Data

(60) Provisional application No. 61/081,536, filed on Jul. 17, 2008.

(51) Int. Cl.
*A61B 5/00* (2006.01)
*A61B 19/00* (2006.01)
*A61F 2/00* (2006.01)
*A61F 7/00* (2006.01)
*G01K 1/08* (2006.01)
*G01K 1/14* (2006.01)
*G01K 13/00* (2006.01)

(52) U.S. Cl.
USPC ........... 600/557; 600/552; 600/555; 607/102; 607/108; 607/111; 374/141; 374/142

(58) Field of Classification Search
USPC ............... 600/549, 552, 553, 555, 557, 587; 601/15, 18, 80; 606/20–31; 607/102, 607/108, 111; 374/141–143
See application file for complete search history.

(56) References Cited

U.S. PATENT DOCUMENTS 4,653,507 A * 3/1987 Laudadio ............. 600/555
5,002,065 A 3/1991 LaCourse et al.
(Continued)

FOREIGN PATENT DOCUMENTS

JP 2005052598 3/2005
WO WO87/07969 12/1987

OTHER PUBLICATIONS

Written Opinion and International Preliminary Report on Patentability for PCT application No. PCT/US2009/004159, Jan. 18, 2011.
Website printout for www.usneurologicals.com, Jul. 4, 2007, 17 pages.
European Search Report for EP application 09798324.1, Dec. 12, 2012.

(Continued)

*Primary Examiner* — Sean Dougherty
*Assistant Examiner* — Devin Henson
(74) *Attorney, Agent, or Firm* — Joseph E. Maenner; Maenner & Associates, LLC (57) ABSTRACT

A neuropathy diagnostic device includes a body having a neutral temperature surface disposed on an exterior of the body, a variable temperature surface disposed on the exterior of the body, and a vibrating surface having a variable vibration amplitude. The vibrating surface extends outwardly from the body. A touch sensor extends outwardly from the body. A processor is disposed within the body. The processor is adapted to set a temperature of the neutral temperature surface, vary a temperature of the variable temperature surface, and vary the vibration amplitude of the vibrating surface.

13 Claims, 5 Drawing Sheets

(56) References Cited

U.S. PATENT DOCUMENTS

| | | | |
|---|---|---|---|
| 5,363,859 A * | 11/1994 | Tuckett et al. | 600/552 |
| 5,373,853 A * | 12/1994 | Assal et al. | 600/555 |
| 7,854,703 B2 * | 12/2010 | Poisner | 600/552 |
| 2007/0191730 A1 | 8/2007 | Speidel | |
| 2009/0227890 A1 * | 9/2009 | Lanfermann et al. | 600/555 |

OTHER PUBLICATIONS

Bertelsmann, F.W. et al., "Thermal discrimination thresholds in normal subjects and in patients with diabetic neuropathy", Journal of Neurology, Neurosurgery, and Psychiatry, 1985, pp. 686-690.

* cited by examiner

NEUROPATHY DIAGNOSTIC DEVICE

CROSS-REFERENCE TO RELATED APPLICATION

The present application is a U.S. National Stage Application of PCT application Ser. No. PCT/US2009/004159, filed on Jul. 17, 2009, which claims priority from U.S. Provisional Patent Application Ser. No. 61/081,536, filed on Jul. 17, 2008, both of which are incorporated by reference in their entireties.

BACKGROUND OF THE INVENTION

Neuropathy is a medical condition where a patient has reduced sensitivity in through-the-skin sensing of temperature variations, vibrations, and tactile stimulation. Neuropathy is common for patients with diabetes. Attention to diabetes has increased significantly as more individuals are being diagnosed with some form of the disease. Early and accurate diagnosis of neuropathies associated with diabetes or other medical issues may lead to earlier treatment to reduce the effect of these issues on the patient.

SUMMARY OF THE INVENTION

Briefly, the present invention provides a neuropathy diagnostic device that includes a body having a neutral temperature surface disposed on an exterior of the body, a variable temperature surface disposed on the exterior of the body, and a vibrating surface having a variable vibration amplitude. The vibrating surface extends outwardly from the body. A touch sensor extends outwardly from the body. A processor is disposed within the body. The processor is adapted to set a temperature of the neutral temperature surface, vary a temperature of the variable temperature surface, and vary the vibration amplitude of the vibrating surface.

BRIEF DESCRIPTION OF THE DRAWINGS

The foregoing summary, as well as the following detailed description of exemplary embodiments of the invention, will be better understood when read in conjunction with the appended drawings, which are incorporated herein and constitute part of this specification. For the purposes of illustrating the invention, there are shown in the drawings exemplary embodiments of the present invention. It should be understood, however, that the invention is not limited to the precise arrangements and instrumentalities is shown. In the drawings, the same reference numerals are employed for designating the same elements throughout the several figures. In the drawings.

DETAILED DESCRIPTION OF THE INVENTION

Although the invention is illustrated and described herein with reference to specific embodiments, the invention is not intended to be limited to the details shown. Rather, various modifications may be made in the details within the scope and range of equivalents of the disclosure without departing from the invention. The invention is best understood from the following detailed description when read in connection with the accompanying drawing figures, which show exemplary embodiments of the invention selected for illustrative purposes. The invention will be illustrated with reference to the figures. Such figures are intended to be illustrative rather than limiting and are included is herewith to facilitate the explanation of the present invention.

Referring to FIGS. 1-4 in general, a neuropathy detection device 100 ("device 100") that is used to diagnose neuropathy in patients is shown. Neuropathy is common for patients with medical issues, such as diabetes or erectile dysfunction. Device 100 includes a body 101 having an exposed neutral temperature surface 102 and an exposed variable temperature surface 104 at one end of body 101, and an exposed vibration surface 106 that extends outwardly from an opposing end of body 101. A filament 108 extends outwardly from body 101. Filament 108 may be a monofilament, such as nylon wire.

A medical professional, such as, for example, a physician, may use device 100 on a patient by touching various locations on the patient's skin with surfaces 102, 104, 106 and/or filament 108. The patient's reaction to these touches may give the physician an indication of a level of neuropathy in the patient, which may in turn aid or enable the physician to diagnose the patient.

Figure 4:
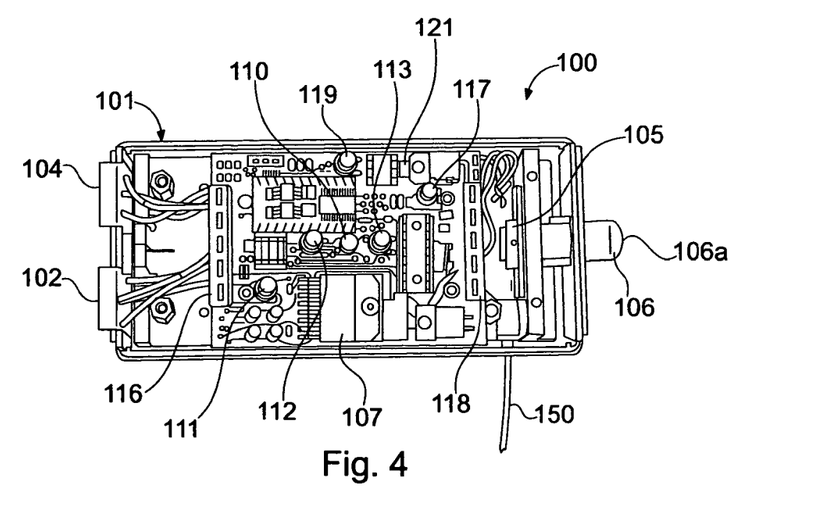
FIG. 4 is a top plan view of the neuropathy detection device of FIG. 1, with the top cover removed.
Figure 5:
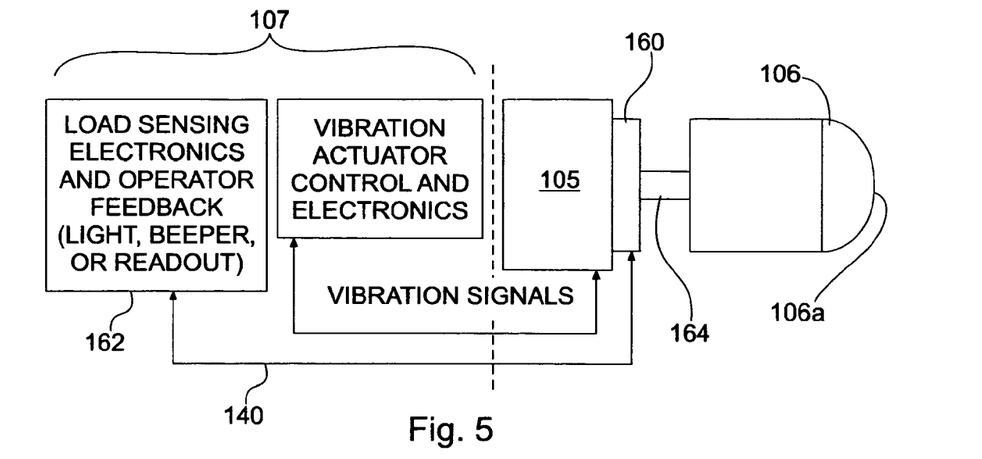
FIG. 5 is a schematic drawing of an exemplary embodiment of a force sensor for a vibrating end effector in the neuropathy detection device of FIG. 1.

Two separate modes of operation are provided for device 100: temperature (using surfaces 102, 104) and vibration (using surface 106), as well as a tactile test (using filament 108). Each mode can be utilized at any time and the operator may switch back and forth between the two modes and/or the tactile test. Controls and indicators are included on s body 101 to allow the operator to control surfaces 102, 104, 106 and to give the operator an indication of the operating parameters of surfaces 102, 104, 106. A controller, such as a microcontroller 107, shown in FIGS. 4 and 5, is used to control operation of surfaces 102, 104, 106.

Figure 1:
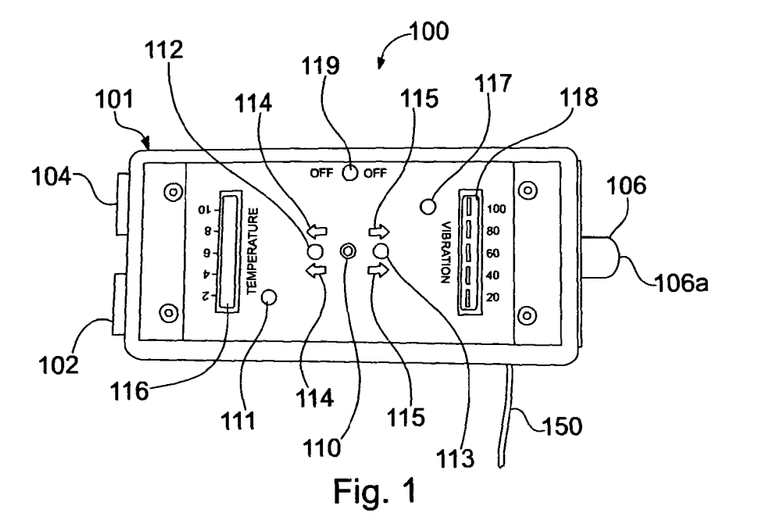
FIG. 1 is a top plan view of a neuropathy detection device according to an exemplary embodiment of the present invention.
Figure 2:
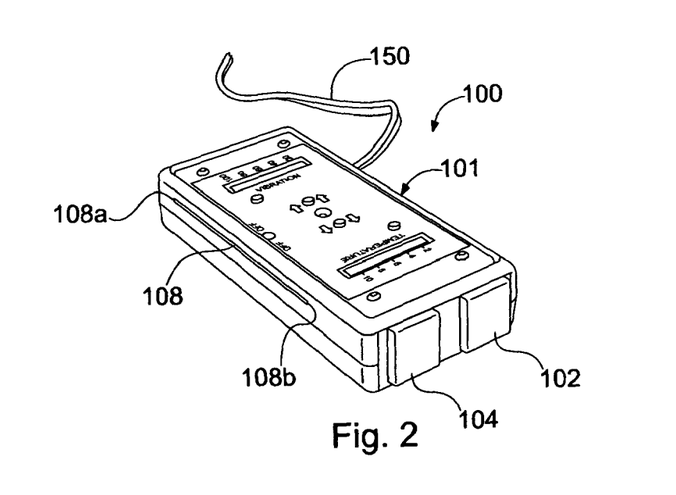
FIG. 2 is a front perspective view of the neuropathy detection device of FIG. 1.

The patient's ability to discern the differences between the temperatures of neutral temperature surface 102 and variable temperature surface 104, positioned at various locations on the patient's skin, gives the physician an indication of the level of neuropathy. Referring specifically to FIGS. 1, 2, and 4, in an exemplary embodiment, neutral temperature surface 102 and variable temperature surface 104 are both generally square, flat pads with sides that are about 1-½ to 2 cm long.

Variable temperature surface 104 may be independently controlled by the operator such that the temperature difference between neutral temperature surface 102 and variable temperature surface 104 varies up to about 10 degrees Celsius. In an exemplary embodiment, neutral temperature surface 102 may be set by controller 107 at about 25 degrees Celsius. Variable temperature surface 104 may be varied at 2 degree increments between a temperature of between about 15 and about 25 degrees Celsius. While in this exemplary embodiment, the temperature of variable temperature surface 104 may be set to be lower than the temperature of neutral temperature surface 102, those skilled in the art will recognize that the temperature of variable surface 104 may be set higher than the temperature of neutral temperature surface 102.

A power indicator LED 110 illuminates when power is provided to device 100. A temperature mode button 111 may be pressed to activate the temperature mode and to provide power to heat surfaces 102, 104. Neutral temperature surface 102 is powered to a fixed temperature, such as, for example, 25 degrees Celsius, and variable temperature surface 104 at a variable temperature in degree increments, such as, for example, increments of 2 degrees Celsius. The operator can control the temperature of variable temperature surface 104 by using increment buttons 112, 113. Arrows 114 on either side of increment button 112 pointing toward surfaces 102, 104 indicate that the operation of increment button 112 raises the temperature difference between neutral temperature surface 102 and variable surface 104, while arrows 115 on either side of increment button 113 pointing away from surfaces 102, 104 indicate that the operation of increment button 113 lowers the temperature difference between neutral temperature surface 102 and variable surface 104. An LED bar graph 116 displays a temperature offset between neutral temperature surface 102 and variable temperature surface 104. An "Off" button 119 turns off device 100.

Temperature variations on surfaces 102, 104 are created through standard solid state thermoelectric devices known as "Peltier Devices." As shown in FIG. 5, a Peltier Device 120 labeled "Steady Peltier" controls neutral temperature surface 102 (shown in FIG. 1), while a Peltier Device 122 labeled "Variable Peltier" controls variable temperature is surface 104 (shown in FIG. 1).

A Peltier Device is essentially a solid state heat pump with no moving parts. A DC voltage is applied to the device, which causes heat to move from one side to the other. This movement of the heat causes an apparent cooling of one side and heating of the other side. Exemplary Peltier Devices used for surfaces 102, 104 may be about 1.25 cm square and about 0.25 cm thick. The direction of heat flow within a Peltier Device can be reversed by simply reversing the polarity of the DC current applied to the device. By constructively controlling the current level and polarity of the current applied to a Peltier Device, a constant temperature can be maintained.

Peltier Devices 120, 122 used in the exemplary embodiment of device 100 may be identical. Each Peltier Device 120, 122 is powered by a separate dual H Bridge 124, 126, respectively. An H bridge has two outputs that can have its output commanded to reverse polarity. An H bridge is either "on" or "off," meaning that the H bridge either delivers full power to the Peltier, or no power. Since it is necessary to set various heat pump levels (and therefore temperature as measured on surfaces 102, 104), controller 107 varies the electrical current levels to H bridges 124, 126. This may be done via pulse width modulation (PWM) which provides a repeated signal of "on" and then "off." The relative time of "off" versus "on" will set, on average, the power going to each Peltier Device 120, 122 and therefore the temperature at surfaces 102, 104, respectively.

Each surface 102, 104 includes a respective temperature sensor 128, 130, which provides feedback to microcontroller 107 via a respective analog to digital (A/D) converter 132, 134.

Figure 3:
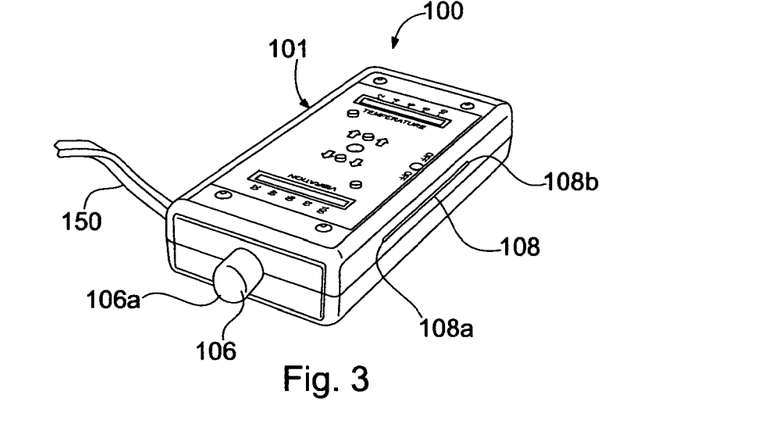
FIG. 3 is a rear perspective view of the neuropathy detection device of FIG. 1.

The patient's ability to discern vibrations at various locations on the patient's skin also gives the physician an indication of the level of neuropathy. Referring specifically to FIGS. 1, 3, and 4, vibration surface 106 may extend outwardly from body 101 and have a generally cylindrical shape with a hemispherical end. Vibration surface 106 may be controlled to vibrate in and out at constant frequency, but with a variable amplitude. In an exemplary embodiment, vibration surface 106 vibrates at a frequency of about 120 Hz, is although other frequencies are also contemplated. The amplitude of vibration of vibration surface 106 may be varied between about 100 percent of full amplitude and about 20 percent of full amplitude. An LED bar graph 118 displays a percentage of vibration amplitude relative to a maximum available amplitude. In an exemplary embodiment, the amplitude may be adjusted in 20 percent increments (100, 80, 60, 40, or 20 percent of full amplitude), although those skilled in the art will recognize that other increments may be used.

As illustrated in FIG. 5, in an exemplary embodiment, vibration for vibrating surface 106 may be provided by a magnetic coil moving a magnet (shown collectively as magnet 105). The magnet 105 may be coupled to vibrating surface 106. A signal from microcontroller 107 to the coil is a constant frequency. A low power signal from microcontroller 107 may be amplified using a simple operational amplifier 136 (shown schematically in FIG. 6) and transistor (not shown). The amplitude of the vibration is also controlled by microcontroller 107. While an exemplary mechanism for vibrating the vibrating surface 106 is shown, those skilled in the art will recognize that other mechanisms may be used.

Referring to FIGS. 1 and 4, increment buttons 112, 113 may be used to adjust the vibration amplitude down or up as desired. Increment button 113 will increase the vibration amplitude, while increment button 112 will decrease the vibration amplitude. "Off" button 119 turns off device 100.

Optionally, as illustrated in FIG. 5, vibration surface 106 may incorporate a pressure sensor 140. Pressure sensor 140 may include a load cell 160 that is electronically coupled to a load sensing electronics component 162 in controller 107 and generates an indication when sufficient pressure is applied by device 100 on the patient's skin. The indication may be an audible indication, such as, for example, a beep, a visual indication such as, for example, a light, or some other suitable type of indication to signify to the user that device 100 is being applied to the patient's skin with sufficient force to enable the patient to sense the vibrations from vibration surface 106. The indicator would operate as is long as the pressure applied to the patient is sufficient to enable the patient to sense the vibrations.

Load cell 160 may be coupled to magnet 105 and disposed between magnet 105 and vibration surface 106. Optionally, as illustrated in FIG. 5, a mechanical extension 164 may couple load cell 160 to vibration surface 106.

Figure 6:
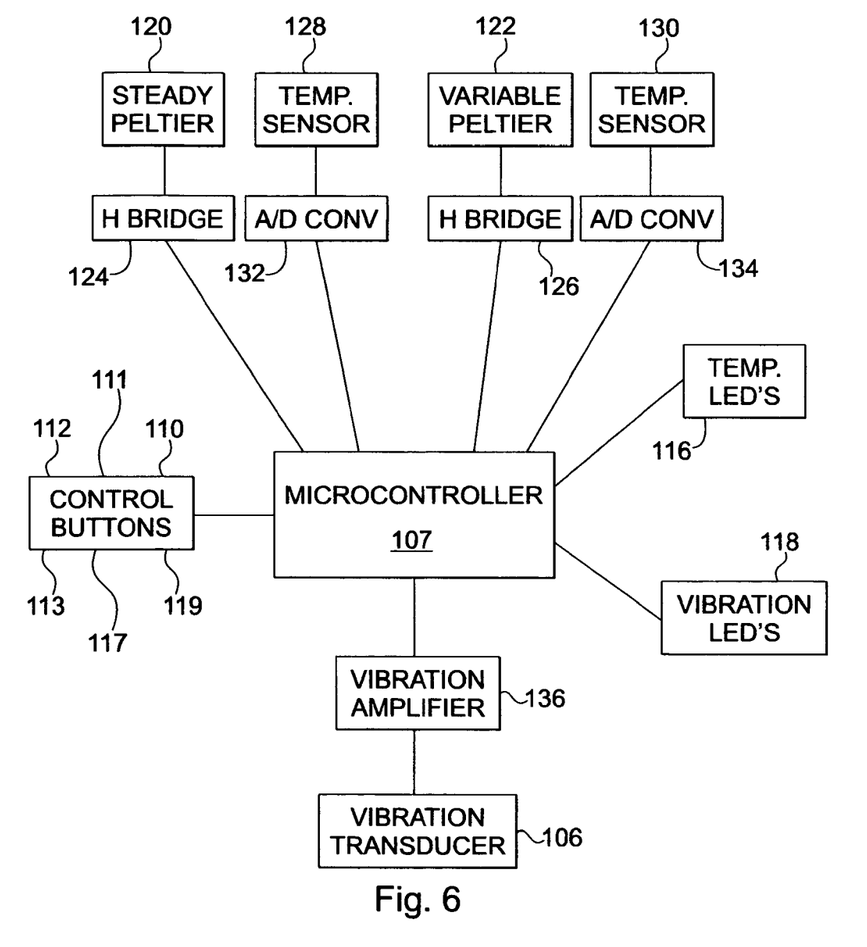
FIG. 6 is a block diagram illustrating a functional layout of a circuit used to operate the neuropathy detection device of FIG. 1.

Referring to the control diagram of FIG. 6, microcontroller 107 may be used to control the temperature of surfaces 102, 104 and the vibration of vibration surface 106. Microcontroller 107 is disposed within body 101 and may be an 8 bit industrial processor with 16 digital inputs and outputs. An associated printed circuit board 121 (shown in FIG. 4) not only contains the circuitry, but also provides the proper layout and mounting for LED's 116, 118 and buttons 110, 111, 112, 113, 117, 119.

Referring to FIGS. 2 and 3, filament 108 provides a touch sensation test. In an exemplary embodiment, the tactile aspect of device 100 utilizes a standard monofilament nylon wire for filament 108, having a free end 108*a*, which is used to check the patient's tactile sensitivity. For protection when not in use, filament 108 may be disposed against the outside of body 101 and can be readily pivoted about a pivoting end 108*b* by the operator at any time. Alternatively, although not shown, filament 108 may be housed within body 101 and pulled out from body 101 when desired. After use, filament 101 may be pushed back into body 101 for storage.

In an exemplary embodiment, device 100 may be powered by standard 110 volt alternating current, stepped down to 6 volt direct current through a transformer. Internally, a 5 volt regulator may be provided to provide voltage to digital components within device 100.

Electrical power may be provided to device 100 through an electrical cord 150, which is partially shown in FIGS. 1-4. Alternatively, device 100 may be powered by batteries (rechargeable or disposable) that are contained within body 101 of device 100.

While body 101 is illustrated in FIGS. 1-4 as a generally rectangular enclosure, those skilled in the art will recognize that body 101 may be other shapes as well, is including, but not limited to, a cylindrically shaped body.

Device 100 may optionally be used to record data obtained during testing. In a first embodiment, device 100 has no storage capacity within itself, but transmits data from microcontroller 107 via radio frequency or other suitable transmission medium to a storage device, such as, for example, a personal/laptop computer. The patient's profile may have already been called up on the storage device and the data transmitted from device 100 is automatically transmitted to the patient's file. The information transmitted from device 100 may include maximum/minimum temperatures and or vibration amplitudes generated by device 100.

Alternatively, device 100 may have memory within microcontroller 107 or coupled to microcontroller 107 and the capability to receive/transmit information. Device 100 may receive patient information uploaded to device 100 from the personal/laptop computer. Device 100 may include an indicator, such as, for example, an LCD or LED screen that displays the patient information so that the operator knows that the correct patient information has been downloaded to device 100. Data obtained during operation of device 100 is then associated with the patient information. This data may be transmitted back to the personal/laptop computer instantly, after all data for the particular patient is obtained, or even after uses with several different patients, such as, for example, at the end s of a work day. Those skilled in the art will recognize that known methods may be used to store and transmit data between device 100 and another device.

Further, if device 100 is battery operated with rechargeable batteries that are recharged by inserting device into a recharging station (not shown), the recharging station may include a port to engage device 100 for downloading data from device 100 into a storage device.

To operate device 100, the operator turns on device 100 by pressing either temperature mode button 111 or vibration mode button 117. The operator can press either mode button 111, 117 at any time to switch between temperature and vibration modes.

To conserve energy (and battery power, if batteries are used), device 100 is times out after 30 seconds on its own if no buttons are pressed. Any adjustment using increment buttons 112, 113 adds a new period of 30 seconds to the timeout mechanism. The operator can add another 30 seconds by simply pressing the appropriate mode button 111, 117. "Off" button 119 may be pressed at any time to shut down device 100 prior to device 100 timing out.

When device 100 is first powered on, device 100 will default to make variable temperature surface 104 have a 2 degree offset from neutral temperature surface 102. At any time, the operator can use increment buttons 112, 113 to adjust this offset. LED bar graph 116 shows the operator which offset is currently being provided by device 100. There is a small delay in attaining the proper temperatures and LED bar graph 116 reflects this situation by blinking while surfaces 102, 104 are brought to their desired temperatures. LED bar graph 116 remains steadily lit when surfaces 102, 104 are at their desired temperature(s). The operator is free to adjust device 100 to any of the preprogrammed offsets based on his need for further tests as dictated by the patient's responses. Device 100 may be programmed to shut itself off if no buttons have been pushed for any desired time level, such as 60 seconds.

If the operator desires to operate the temperature mode first, the operator presses temperature mode button 111. Device 100 will begin to appropriately heat or cool both temperature surfaces 102, 104. Device 100 will always attempt to make neutral temperature surface 102 stay at 25 degrees Celsius. If no other action is taken by the operator, device 100 will attempt to make variable temperature pad 104 two (2) degrees below the temperature of neutral temperature surface 102. LED bar graph 116 will blink at "−2" while device 100 works to acquire the proper temperature, and will become steady when the proper temperatures on both surfaces 102, 104 (i.e., a temperature difference of 2 degrees Celsius between surfaces 102, 104) are reached. Increment buttons 112, 113 may be used to increase or decrease the temperature differential. With each change in desired offset, LED bar graph 116 moves to represent the new differential. The corresponding LED on LED bar graph 116 will blink while device 100 is working to achieve the new is temperature goal and will remain steady when the proper temperatures have been reached.

When LED bar graph 116 is illuminating in steady state, the operator then applies surfaces 102, 104 simultaneously to an area on the patient's skin surface. The operator then asks for the patient's feedback depending on whether the patient could sense the temperature offset between surfaces 102, 104. This offset may first be set to the lowest amount (e.g., 2 degrees) and may then be incremented to larger offset values. In an exemplary embodiment, each increment makes variable surface 104 two (2) degrees cooler. Once the patient reports that he/she can feel the offset, the operator then knows the patient's temperature offset detection level for that particular part of the body.

In addition to temperature testing, the operator may also perform a vibration study. The operator presses vibration mode button 117, activating vibration mode, causing vibration surface 106 to vibrate at 120 Hz, and at 100% of the amplitude of vibrating surface 106. The operator may use increment buttons 112, 113 to adjust the vibration amplitude down or up as desired. Increment button 113 will increase the vibration amplitude, while increment button 112 will decrease the vibration amplitude. As noted earlier with respect to the temperature mode, device 100 shuts down after 30 seconds if no additional inputs are provided. Any adjustment to the amplitude via increment buttons 112, 113 will reset the 30 second clock.

The operator touches an end 106a of vibration surface 106 to the area of interest on the patient's body. Load cell 160 transmits a signal to load sensing electronics component 162, which transmits a signal (e.g., light, audible, etc.) to the operator to let the operator know that vibration surface 106 is engaging the patient with sufficient force. With vibration surface 106 vibrating, the patient may react by stating whether or not he/she can feel the vibration. The operator may then decrease the amplitude of the vibration and obtain further patient feedback to discern where the patient's threshold limit of detection may be. The operator can freely move vibration amplitude up and down as desired, with the changes in amplitude happening virtually instantaneously.

The operator may also perform a tactile study. Filament 108 may be moved is away from body 101 by rotating filament 108 about pivoting end 108*b* to allow free end 108*a* of filament 108 to extend away from body 101. Free end 108*a* may be gently pressed into the skin of the patient to determine the patient's sensation of filament 108 being pressed into the skin.

While an operating sequence of temperature, vibration, and touch using device 100 is described above, those skilled in the art will recognize that device 100 may be used in any other appropriate order, and in any combination of tests.

Figure 7:
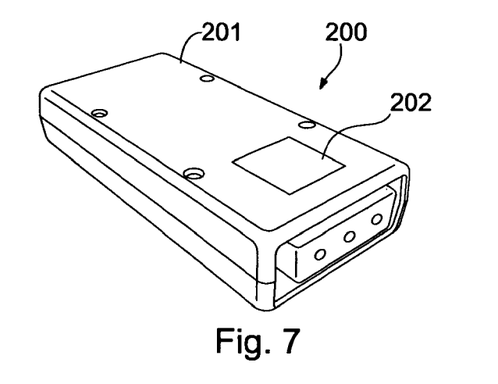
FIG. 7 is a top perspective view of a neuropathy detection device according to an alternative exemplary embodiment of the present invention.
Figure 8:
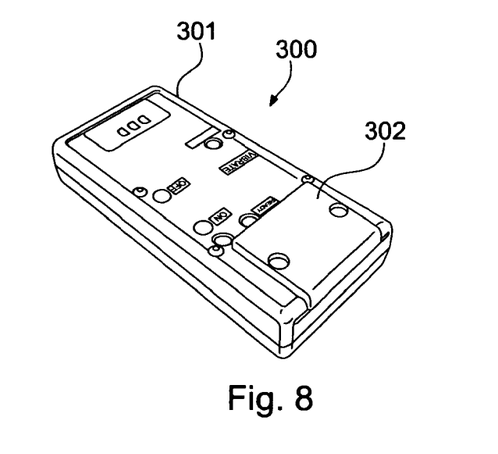
FIG. 8 is a top perspective view of a neuropathy detection device according to another alternative exemplary embodiment of the present invention.

Alternative embodiments of devices 200, 300 according to the present invention are illustrated in FIGS. 7 and 8, respectively. Devices 200, 300 incorporate temperature surfaces on opposing sides of body 201, 301, respectively. In FIGS. 6 and 7, only neutral surfaces 202, 302 are shown, with variable temperature surfaces, not shown, being located on the underside of body 201, 301 respectively. In device 200, neutral surface 202 is flush with body 201, while in device 300, neutral surface 302 extends outwardly from body 301.

Although the invention is illustrated and described herein with reference to specific embodiments, the invention is not intended to be limited to the details shown. Rather, various modifications may be made in the details within the scope and range of equivalents of the claims and without departing from the invention. For example, device 100 may include three or more temperature surfaces. Alternatively, or in addition, device 100 may include two or more vibration surfaces, each capable of operating at different amplitudes and/or frequencies, or with different geometries to vary the amount of surface area in contact with the patient.

What is claimed:

1. A neuropathy diagnostic device comprising:
   a body having a first side and a second side opposite the first side, the body further comprising:
   a neutral temperature surface extending outwardly from the first side;
   a variable temperature surface extending outwardly from the second side; and
   a vibration surface having a variable vibration amplitude and extending outwardly from the body between the first side and the second side; and
   a processor disposed within the body, wherein the processor is adapted to set a temperature of the neutral temperature surface, vary a temperature of the variable temperature surface, and vary the vibration amplitude of the vibration surface.

2. The neuropathy diagnostic device according to claim 1, wherein the variable temperature surface is variable between a first temperature less than the neutral temperature surface and a second temperature greater than the neutral temperature surface.

3. The neuropathy diagnostic device according to claim 2, wherein the variable temperature surface is incrementally variable by about two degrees below the neutral temperature surface.

4. The neuropathy diagnostic device according to claim 2, wherein the variable temperature surface is incrementally variable by about two degrees above the neutral temperature surface.

5. The neuropathy diagnostic device according to claim 1, wherein the vibration surface comprises a pressure sensor.

6. The neuropathy diagnostic device according to claim 5, wherein the pressure sensor is coupled to an indicator for indicating sufficient pressure applied by the pressure sensor to a surface.

7. The neuropathy diagnostic device according to claim 1, further comprising an output for recording data generated by each of the neutral temperature surface, the variable temperature surface, and the vibration surface.

8. The neuropathy diagnostic device according to claim 1, further comprising a touch sensor extending outwardly from the body.

9. The neuropathy diagnostic device according to claim 1, wherein the device is handheld.

10. The neuropathy diagnostic device according claim 1, wherein the body comprises a single handheld body.

11. A neuropathy diagnostic device comprising:
    a body having:
    a neutral temperature surface extending outwardly from the body;
    a variable temperature surface extending outwardly from the body; and
    a vibration surface having a variable vibration amplitude, the vibration surface extending outwardly from the body;
    a processor disposed within the body, wherein the processor is adapted to set a temperature of the neutral temperature surface, vary a temperature of the variable temperature surface, and vary the vibration amplitude of the vibration surface; and
    a first button operatively coupled to the processor to alternatively vary one of the temperature of the variable temperature surface and the vibration of the vibration surface in only a first direction; and
    a second button operatively coupled to the processor to alternatively vary the one of the temperature of the variable temperature surface and the vibration of the vibration surface in only a second direction.

12. The neuropathy diagnostic device according claim 11, wherein the body comprises a single body.

13. A neuropathy diagnostic device comprising:
    a body having a first side and a second side, the body further comprising:
    a neutral temperature surface extending outwardly from the first side;
    a variable temperature surface extending outwardly from the first side; and
    a vibration surface having a variable vibration amplitude and extending outwardly from the second side; and
    a processor disposed within the body, wherein the processor is adapted to set a temperature of the neutral temperature surface, vary a temperature of the variable temperature surface, and vary the vibration amplitude of the vibration surface.

\* \* \* \* \*